United States Patent [19]

Baumel et al.

[11] 4,261,340
[45] Apr. 14, 1981

[54] ARTIFICIAL ANUS OBTURATING DEVICE

[75] Inventors: Hugues Baumel; Pierre Rabischong, both of Montpellier; Jean Loygue, Paris, all of France

[73] Assignee: Laboratories Biotrol S.A., Paris, France

[21] Appl. No.: 11,866

[22] Filed: Feb. 13, 1979

[30] Foreign Application Priority Data

Feb. 21, 1978 [FR] France .................................. 78 04959

[51] Int. Cl.³ .............................................. A61B 19/00
[52] U.S. Cl. ............................ 128/1 R; 128/DIG. 25
[58] Field of Search ........ 128/1 R, 1.3, 283, DIG. 25; 3/1; 132/53

[56] References Cited

U.S. PATENT DOCUMENTS

| 2,243,529 | 5/1941 | Grossman et al. | 128/1 R |
| 3,516,422 | 6/1970 | Bechtold et al. | 132/53 |
| 3,565,073 | 2/1971 | Giesy | 128/283 |
| 3,811,425 | 5/1974 | Widdifield | 128/330 X |
| 3,952,726 | 4/1976 | Hennig et al. | 128/1 R |

Primary Examiner—Dalton L. Truluck
Attorney, Agent, or Firm—Berman, Aisenberg & Platt

[57] ABSTRACT

The invention relates to an artificial anus obturating device.

The device according to the invention includes a magnetic peri-orificial plate (3) provided on one of its surfaces with an adhesive coating (5), and a flexible plug lodgeable in the intestinal opening and essentially constituted by a hollow cylindrical body (6) provided at its end turned towards the outside of the abdomen with a magnetic ring (7) which surrounds it and, when said plug is in the intestinal opening, cooperates with the peri-orificial plate to obturate the artificial anus, the said cylindrical body including, at its opposite end turned towards the intestine, slots (12) for the passage of gases, the cavity of said cylindrical body being closed at its outer end by a suitable closure device provided with one or several slots (14) for the passage of gases.

17 Claims, 3 Drawing Figures

ARTIFICIAL ANUS OBTURATING DEVICE

The present invention relates to an artificial anus obturating device.

Enterostomized patients, in particular colostomized patients, have an intestinal opening in the abdominal wall. Three types of solutions for closing such an intestinal opening are at present available to such patients.

The first of these solutions consists of gluing an adhesive pocket two to three times daily on the abdominal skin, opposite the intestinal opening, to collect the stools.

Another solution consists of positioning a transfer plate on the abdominal wall. This plate remains in position much longer than the pockets which are glued to it. This device is particularly well suited to patients with an irritable skin.

Recently, a true plug has been proposed which is suitable for closing the intestinal opening of colostomized or ileostomized patients. Reference may be made to French Pat. No. 74 42 079 which describes such a device. This device is constituted by a permanent magnet, adapted to be positioned in the region of the intestinal opening, and one or several other weak magnets or magnetic elements which cooperate with said permanent magnet to close the intestinal opening. The permanent magnet may be of annular shape and must be implanted under the intestinal wall around the opening. The other portion of this device may, according to another embodiment, be an obturating cap constituted by an annular magnet similar to the permanent magnet and a central magnet placed in the projecting portion of said cap and which is located in the intestine when this obturating device is in position.

Such a device must be placed in position in the course of a surgical operation, for example, in the course of the forming of the stomy, and its possible withdrawal would necessitate another surgical operation. This device is heavy, irreversible, and generally reserved for newly operated patients, but it cannot be applied in all cases. In addition, the pinching of the skin around the anastomosis has drawbacks. Besides, it is not possible to lodge a magnetic ring indiscriminately at any place into the abdomen.

It is also known, for example from U.S. Pat. No. 3,565,073, to attach a material receiving appendage to the skin of an animal by means of stiff magnetic elements, one of which has to be buried or embedded beneath the skin.

A novel device, which is light, comfortable, of little traumatic effect and usable by almost all operated patients, notably colostomized patients, for obturating the intestinal opening has now been perfected. In addition, neither the placing nor the withdrawal of the device according to the invention requires a surgical operation and the patient who abandons the above-mentioned types of solution for the device according to the invention could subsequently reutilize the abandoned device without delay, or inconvenience of any sort, except if this device is that according to the aforesaid French Pat. No. 74 42 079, in which case a surgical operation would be necessary for positioning the latter as has been previously indicated. Due to its characteristics, this new device has great flexibility in use.

From its general aspect, the invention relates to a device for obturating an artificial anus, which essentially comprises:

(1) a magnetic peri-orificial plate, which is applied to the abdominal wall, (2) a flexible plug constituted by a substantially cylindrical body provided at its upper end with a magnetic plate which surrounds it and, when said plug is in the intestinal opening, cooperates with the magnetic peri-orificial plate to effect the closing of the artificial anus.

By magnetic material there is intended herein any magnetic-susceptible material, i.e. either a magnetized material or a material attractable by a magnet with the proviso that both magnetic elements of the device should be made of materials selected appropriately for providing magnetic attraction with each other.

The device according to the invention therefore essentially comprises:

(1) a magnetic peri-orificial plate provided on one of its surfaces with an adhesive coating, (2) a flexible plug lodgeable in the intestinal opening and constituted by a hollow cylindrical body provided, at its end turned towards the outside of the abdomen, with a magnetic plate which surrounds it and, when said plug is in the intestinal opening, cooperates with a peri-orificial plate to effect the closure of the artificial anus, said cylindrical body including (at its opposite end turned towards the intestine) slots for the passage of gases, the cavity of said cylindrical body being closed at its outer end by a suitable closure device provided with one or several slots for the passage of gases.

It should be noted that, in service, the plug can be replaced with a disposable bag designed for collecting the waste matter leaving the body and provided with an appropriate magnetic peri-orificial plate.

The invention will now be described in more detail with reference to the accompanying drawings, which represent certain embodiments selected by way of illustration but to be considered in no way as limiting, and in which.

Figure 1:
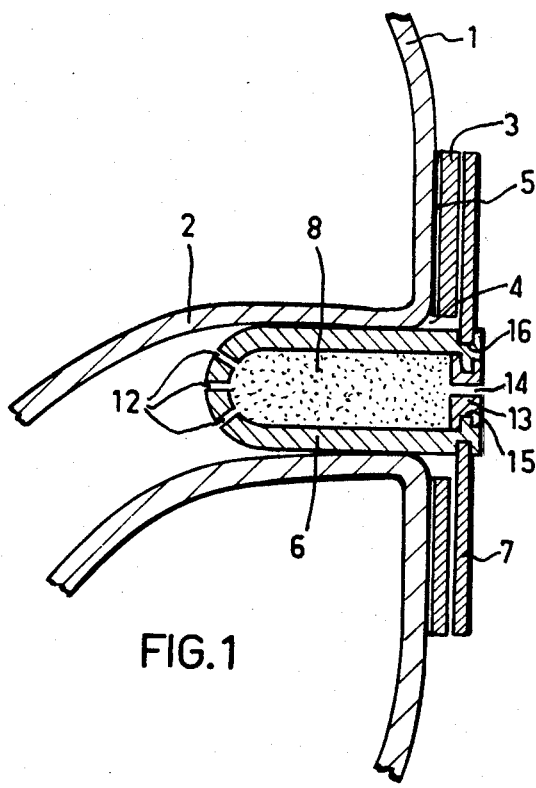
FIG. 1 is a diagrammatic view in section of the device according to the invention, positioned suitably on the patient.

Referring now to the drawings, in FIG. 1, the abdominal wall is denoted by 1 and the intestinal wall by 2. The peri-orificial plate 3 is placed on the abdominal wall around the intestinal opening 4. This plate may have any shape, provided that its central portion is hollow, with the cavity corresponding to the size of the intestinal opening. This plate is constituted by a flexible magnetic material, such as a sheet of natural or synthetic elastomer or copolymer containing magnetic particles, for example ferrite. It is coated on at least one of its surfaces with an adhesive opening 5 which permits its fixing to the abdominal wall. The plug is constituted by a cylindrical body 6 which is provided at its upper part with a magnetic plate 7 surrounding it and whose shape is similar to that of the peri-orificial plate. For greater convenience, in the present description reference will be made to the peri-orificial plate and to the magnetic crown of the plug, it being understood that these parts may be plates of any shape, suitably perforated. The cylindrical body 6 of the plug is hollow. The cavity 8 of this cylindrical body may be filled with at least one material selected from the group consisting of filtering materials and deodorants, this being a preferred embodiment of the device according to this invention.

Figure 2:
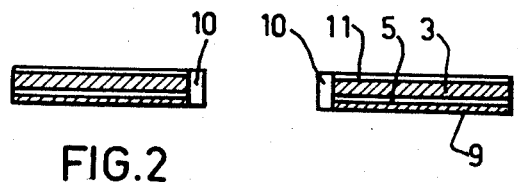
FIG. 2 is a sectional view of the peri-orificial plate according to an embodiment of the device according to the invention.
Figure 3:
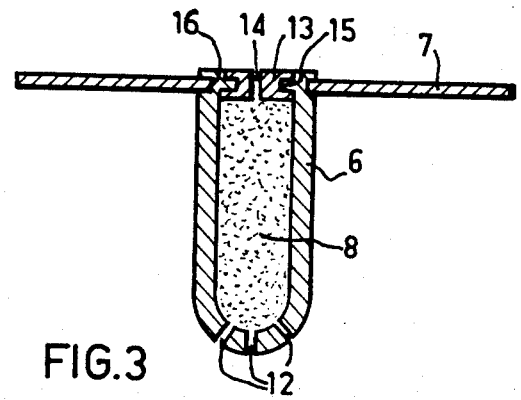
FIG. 3 is a sectional view of the plug according to an embodiment of the device of this invention.

The various elements of the device according to the invention will now be described with reference to FIGS. 2 and 3 which provide an illustration of preferred embodiments of the device according to the invention.

The peri-orificial plate 3 can include on one of its surfaces an adhesive coating or a double surface adhesive 5; this adhesive coating must not irritate the skin; it is, for example, a natural or synthetic adhesive, such as a natural latex.

The adhesive coating 5 can include a protective film 9, which should be pulled away before the peri-orificial plate is set in position. The peri-orificial plate 3 advantageously includes, in its central cavity, a material 10 intended to absorb humidity and secretions of the abdominal mucous membrane, such as a cotton gauze wick or any other appropriate absorbing and/or deodorizing material.

The upper portion of the peri-orificial plate 3 may also include a flexible coating 11 designed to ensure good fluid-tightness, together with the cylindrical body 6. This coating may be constituted, for example, by a silicone elastomer.

The plug of the device according to the invention includes, as has previously been indicated, a cylindrical body 6 with a cavity 8, and it is provided at its upper part with a magnetic crown 7. The cylindrical body 6 includes a groove 16 and the crown or ring 7 may be fixed to the cylindrical body 6 by any other suitable means whatever. The cylindrical body includes at its lower part, which advantageously has a rounded shape, slots 12 which enable the passage of gases from the intestine to the outside. The size of these slots must be such that the filtering material and/or the deodorant, contained in the cavity 8, cannot be released in the intestine. The cavity 8 of the cylindrical body is closed by a closure device 13 provided with one or several slots 14 to enable the evacuation to the outside of the gases emitted by the intestine. This closure device may be held in the cylindrical body 6 by means of the shoulder 15 with which the inside of the cylindrical body 6 is provided.

This mode of fixing the closure device 13 to the cylindrical body 6 is given only by way of example; those with an ordinary skill in the art will understand that any other suitable closure device whatever may be used, with the proviso that the latter should be provided with one or several adequate slots 14. In the same way, as for the slots 12, the slot or slots 14 must not permit the release of the filtering material and/or of the deodorant to the outside.

The above construction is advantageous, since it enables exchange of the body 6 when the material which it contains must be renewed, the other elements of the device remaining usable.

The crown of the plug is constituted by a flexible magnetic material, such as a natural or synthetic rubber or a copolymer containing ferrite particles.

The cylindrical body 6 of the plug is of a flexible non-magnetic material, such as a natural synthetic elastomer, for example, of rubber or of a silicone elastomer.

The filtering material may be, for example, carbon powder or any other suitable conventional filtering agent.

The magnetization of the peri-orificial plate, as well as the magnetization of the ring of the plug, when the same are magnetized, may be unipolar or multipolar, and in straight, circular concentric or radial lines.

The device according to the invention has been described with reference to the appended figures which illustrate embodiments of the invention to which may be added any modification within the scope of the technician skilled in the art, any such modification falling also within the scope of this invention.

The device according to the invention has numerous advantages. Due to the flexibility of the elements applied, it is possible in fact to adapt the device to particular needs relating both to the patient himself (child or adult; thin or fat patient) and to the place where the anostomosis is formed.

In addition, the positioning or removal of such a device may be effected by the patient himself; thus, it could be temporarily abandoned, either for reasons of examination, in which case the collection is done in conventional pockets, or in order to relax the skin. The device according to the invention hence offers the possibility of temporary utilization, and even of trial use.

We claim:
1. An obturation device which consists essentially of
   (a) a magnetic peri-orificial plate,
   (b) a flexible plug having a hollow and substantially cylindrical body with an open end and a closed end,
   (c) a second magnetic plate in the form of a crown or ring which has a shape similar to that of the peri-orificial plate and is attached to and surrounds the flexible plug at a position at or near the open end thereof,
   (d) a closure for the open end of the cylindrical plug, and
   (e) removable and renewable filler material in the cylindrical body;
   said magnetic peri-orificial plate being in a position between the second magnetic plate and the closed end of the flexible plug and having opposed substantially planar surfaces, one of which has an adhesive coating and the other of which is magnetically held in direct contact with a substantially planar surface of said second magnetic plate;
   the flexible plug being capable of extending through the peri-orificial plate and concurrently being lodged in an intestinal opening, having slots in the closed end for passage of gases and being closed at the open end by the closure, and
   the closure having one or several slots for passage of gases.
2. A device according to claim 1 wherein the filler material comprises filtering material.
3. A device according to claim 1 wherein the filler material comprises deodorizing material.
4. A device according to claim 1 wherein the filler material comprises means for absorbing humidity and mucous membrane secretion.
5. In an obturation device, for an artificial anus in an abdominal wall, which comprises:
   (a) a magnetic peri-orificial plate with a central opening,
   (b) a flexible plug capable of being lodged in an intestinal opening, and
   (c) a magnetic ring;
   the improvement wherein:
   the flexible plug has a hollow and substantially cylindrical body with a closed end and an open end and which is adapted to fit through the central opening in the peri-orificial plate; the closed end has slot means for passing gases; the open end has a closure with one or several slots for passing gases and is secured to and surrounded by the magnetic ring; and the hollow body contains at least one filler means selected from the group consisting of filtering material, deodorizing material and material for absorbing humidity and mucous membrane secretion;

said magnetic ring magnetically cooperates with the peri-orificial plate to effect closing the artificial anus when the flexible plug is lodged in the intestinal opening; and said peri-orificial plate has opposed surfaces, one of which is coated with adhesive means to secure it exteriorly to the abdominal wall surrounding the artificial anus.

6. A device according to claim 5 wherein the plate and ring are correspondingly magnetized in a multipolar manner.

7. A device according to claim 6 wherein the plate and ring are correspondingly magnetized in radial lines.

8. A device according to claim 7 wherein the filler means comprises filtering material.

9. A device according to claim 7 wherein the filler means comprises deodorizing material.

10. A device according to claim 7 wherein the peri-orificial plate includes on one of its surfaces a double-faced adhesive coating and on the other surface a flexible silicon-elastomer coating.

11. A device according to claim 7 wherein the peri-orificial plate has, in its central opening, means to absorb humidity and mucous-membrane secretion.

12. A device according to claim 7 wherein the peri-orificial plate is of a flexible magnetic material.

13. A device according to claim 12 wherein the magnetic material is a ferrite-particle containing member selected from the group consisting of a rubber and a copolymer.

14. A device according to claim 7 wherein the ring is composed of a flexible magnetic material.

15. A device according to claim 5 wherein the peri-orificial plate and the magnetic ring are magnetized in unipolar or multipolar manner, along straight, circular concentric, or radial lines.

16. A device according to claim 7 wherein the cylindrical body has a groove in which the magnetic ring is secured.

17. A device according to claim 7 wherein the cylindrical body has an inside shoulder at the open end which permits fastening the closure.

* * * * *